(12) United States Patent
Akagi et al.

(10) Patent No.: US 11,016,087 B2
(45) Date of Patent: May 25, 2021

(54) IMPLEMENT FOR INSPECTION, INSPECTING DEVICE AND INSPECTING METHOD

(71) Applicants: SEKISUI CHEMICAL CO., LTD., Osaka (JP); UNIVERSITY PUBLIC CORPORATION OSAKA, Osaka (JP)

(72) Inventors: Yoshinori Akagi, Osaka (JP); Nobuhiko Inui, Osaka (JP); Kazuhiko Imamura, Osaka (JP); Takamasa Kouno, Osaka (JP); Shigeru Nomura, Osaka (JP); Tatsuro Endo, Sakai (JP)

(73) Assignees: SEKISUI CHEMICAL CO., LTD., Osaka (JP); UNIVERSITY PUBLIC CORPORATION OSAKA, Osaka (JP)

( * ) Notice: Subject to any disclaimer, the term of this patent is extended or adjusted under 35 U.S.C. 154(b) by 24 days.

(21) Appl. No.: 16/076,637

(22) PCT Filed: Feb. 9, 2017

(86) PCT No.: PCT/JP2017/004680
§ 371 (c)(1),
(2) Date: Aug. 8, 2018

(87) PCT Pub. No.: WO2017/138595
PCT Pub. Date: Aug. 17, 2017

(65) Prior Publication Data
US 2019/0041337 A1 Feb. 7, 2019

(30) Foreign Application Priority Data

Feb. 9, 2016 (JP) .............................. JP2016-022465

(51) Int. Cl.
*G01N 33/551* (2006.01)
*G01N 33/543* (2006.01)
(Continued)

(52) U.S. Cl.
CPC ... *G01N 33/54373* (2013.01); *G01N 21/4788* (2013.01); *G01N 21/77* (2013.01);
(Continued)

(58) Field of Classification Search
CPC ............. G01N 33/54373; G01N 21/82; G01N 21/4788; G01N 33/579; G01N 2021/7773
(Continued)

(56) References Cited

U.S. PATENT DOCUMENTS

| 4,661,460 A | 4/1987 | Sakuma |
| 8,298,834 B2 * | 10/2012 | Glezer .................. B01L 3/5025 436/518 |

(Continued)

FOREIGN PATENT DOCUMENTS

| CN | 101473227 A | 7/2009 |
| CN | 101825629 A | 9/2010 |

(Continued)

OTHER PUBLICATIONS

International Search Report for the Application No. PCT/JP2017/004680 dated Mar. 28, 2017.
(Continued)

*Primary Examiner* — Christopher L Chin
(74) *Attorney, Agent, or Firm* — Cheng Law Group, PLLC

(57) ABSTRACT

Provided is an implement for inspection capable of measuring the concentration of a test substance with high accuracy. The implement for inspection according to the present invention is an implement for inspection used for measuring the concentration of a test substance that includes a compound for reacting with a test substance to form a granular substance or a compound which is for being bound to the test substance and is a granular substance, and a wall portion having a periodic structure on its surface.

8 Claims, 8 Drawing Sheets

(51) Int. Cl.
  *G01N 33/579* (2006.01)
  *G01N 21/82* (2006.01)
  *G01N 21/47* (2006.01)
  *G01N 21/77* (2006.01)
(52) U.S. Cl.
  CPC ........... *G01N 21/82* (2013.01); *G01N 33/579* (2013.01); *G01N 2021/7773* (2013.01)
(58) Field of Classification Search
  USPC .............. 436/533, 534, 809, 805; 422/82.11; 435/288.7
  See application file for complete search history.

(56) References Cited

U.S. PATENT DOCUMENTS

| | | | | |
|---|---|---|---|---|
| 2009/0079976 | A1* | 3/2009 | Cunningham | G01N 21/7743 356/246 |
| 2009/0286325 | A1 | 11/2009 | Tanigami et al. | |
| 2010/0046902 | A1* | 2/2010 | Kaplan | G02B 1/005 385/129 |
| 2011/0124036 | A1 | 5/2011 | Yabusaki | |
| 2013/0078150 | A1 | 3/2013 | Obata | |
| 2015/0268237 | A1* | 9/2015 | Kerimo | G01N 33/54373 435/7.1 |
| 2016/0061823 | A1 | 3/2016 | Yokoyama et al. | |

FOREIGN PATENT DOCUMENTS

| | | |
|---|---|---|
| CN | 101389960 B | 3/2013 |
| CN | 104220862 A | 12/2014 |
| JP | 57-66762 U | 10/1982 |
| JP | 60-86468 A | 5/1985 |
| JP | 62-255852 A | 11/1987 |
| JP | 2001-201505 A | 7/2001 |
| JP | 2005-516210 A | 6/2005 |
| JP | 2007-327946 A | 12/2007 |
| JP | 2008-2948 A | 1/2008 |
| JP | 2008-51715 A | 3/2008 |
| JP | 2010-32436 A | 2/2010 |
| JP | 2011-257156 A | 12/2011 |
| JP | 2012-98272 A | 5/2012 |
| WO | WO-03/064995 A2 | 8/2003 |
| WO | WO-2007/076023 A2 | 7/2007 |

OTHER PUBLICATIONS

Written Opinion of the International Searching Authority (PCT/ISA/237) for Application No. PCT/JP2017/004680 dated Mar. 28, 2017.

Written Opinion of the International Searching Authority (PCT/ISA/237) for Application No. PCT/JP2017/0041680 dated Mar. 28, 2017 (English Translation dated Aug. 23, 2018).

Supplementary European Search Report for the Application No. EP 17 750 316.6 dated Aug. 8, 2019.

The First Office Action for the Application No. 201780010615.4 from The State Intellectual Property Office of the People's Republic of China dated Dec. 8, 2020.

* cited by examiner

[FIG. 1]
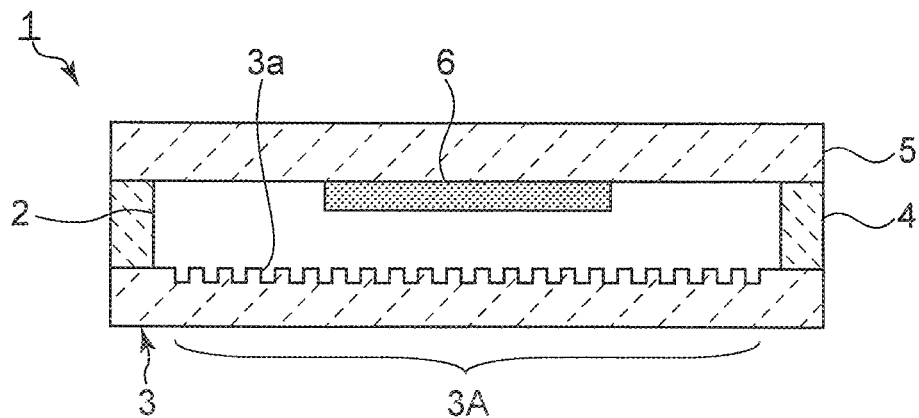
[FIG. 2]
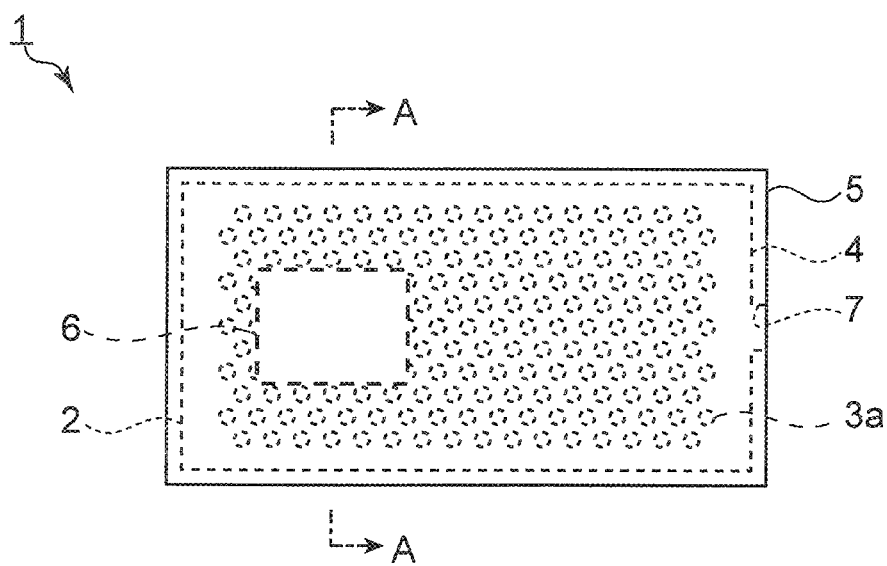
[FIG. 3]
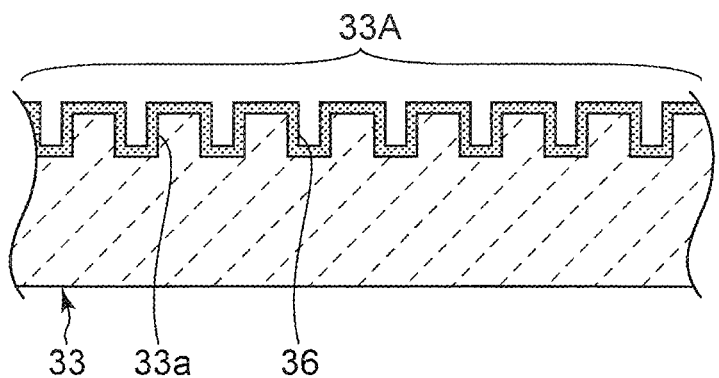

[FIG. 4]
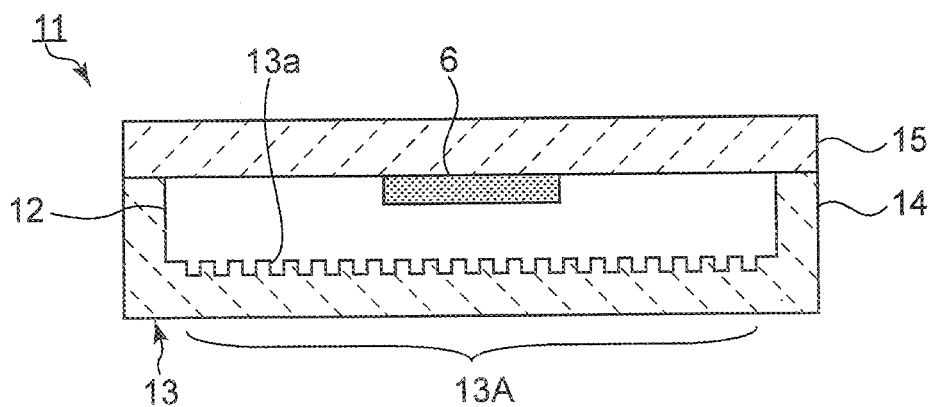
[FIG. 5]
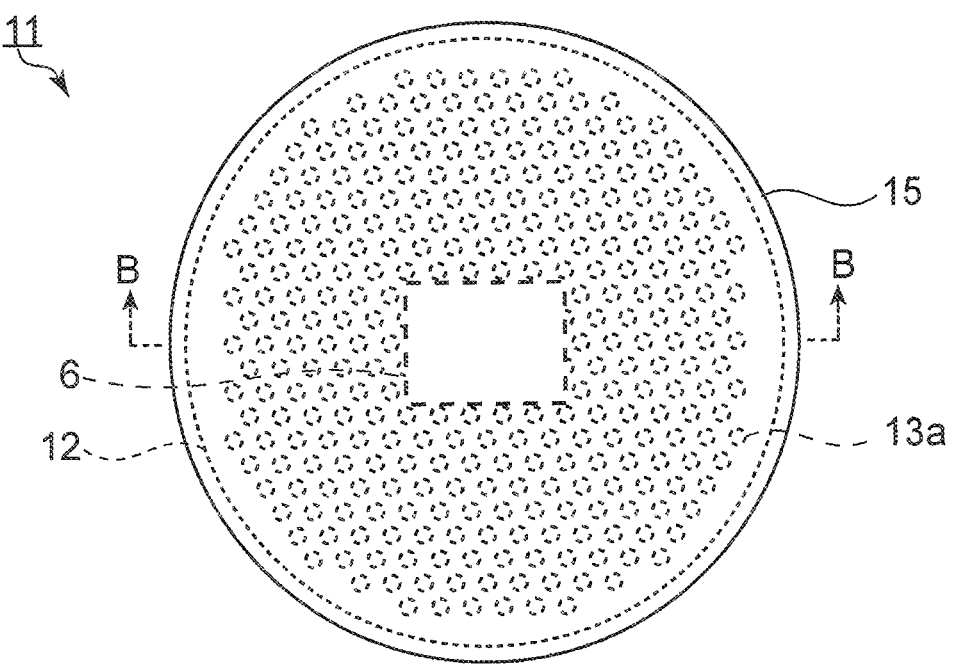

[FIG. 6]
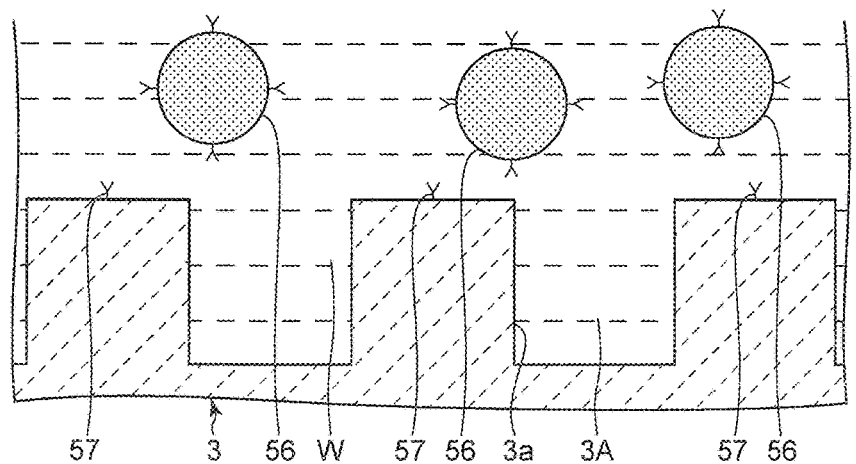
[FIG. 7]
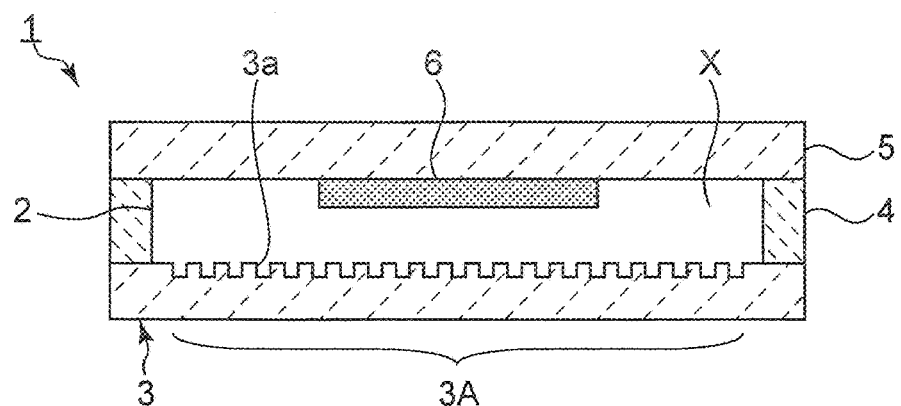
[FIG. 8]
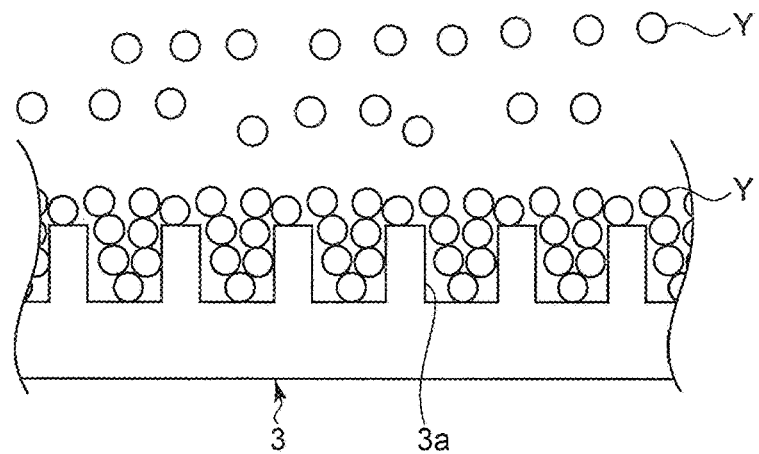

[FIG. 9]
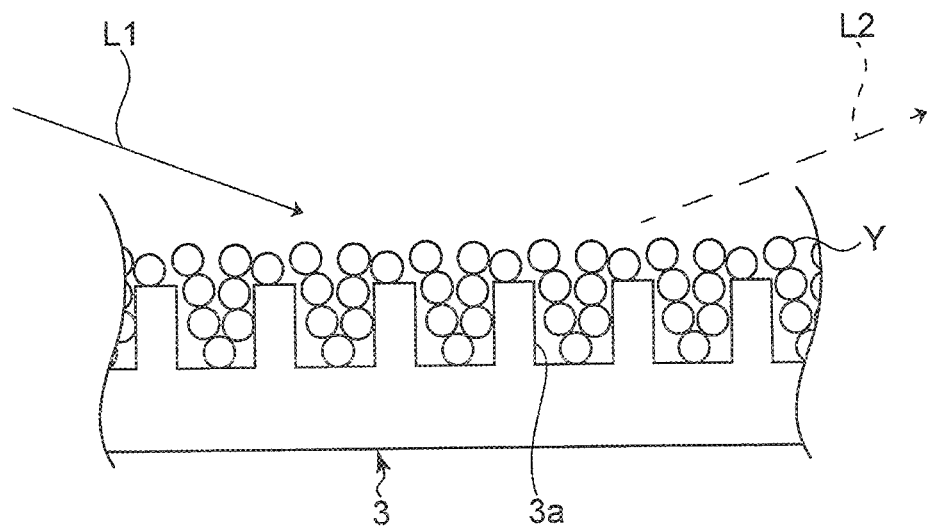
[FIG. 10]
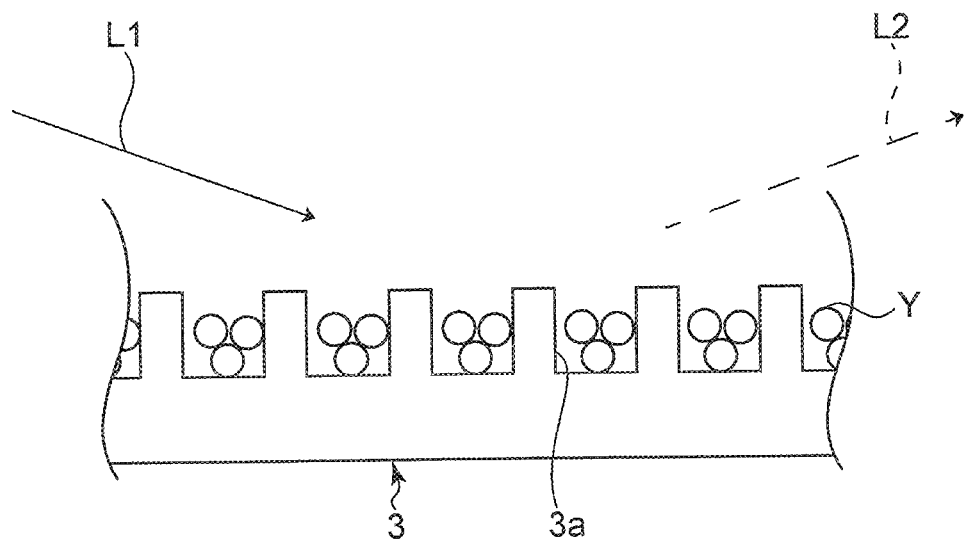

[FIG. 11]
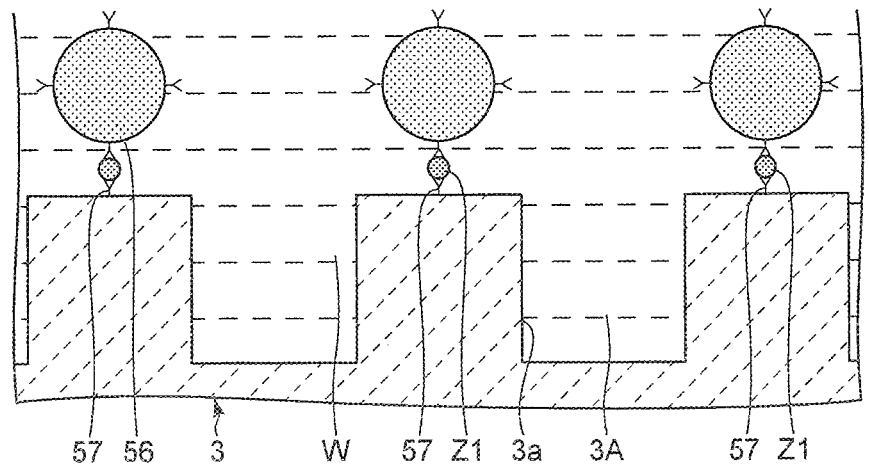
[FIG. 12]
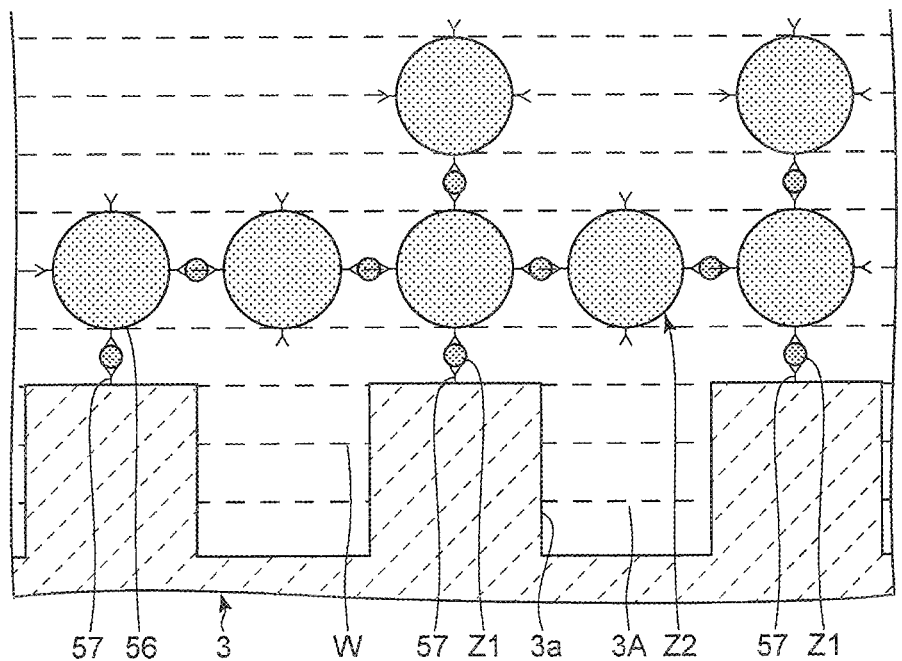
[FIG. 13]
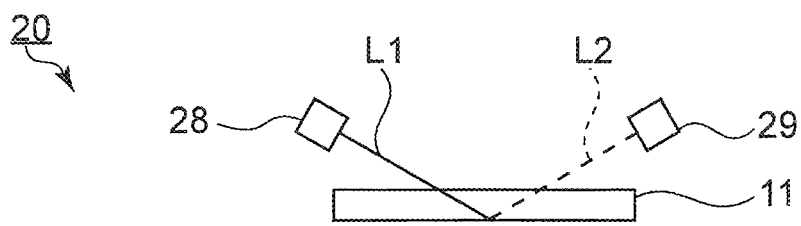

[FIG. 14]
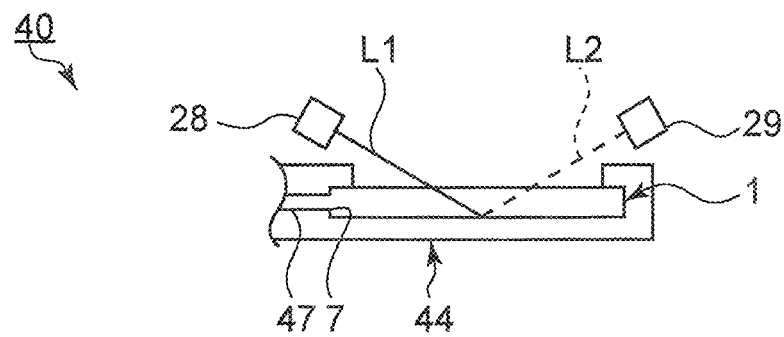
[FIG. 15]
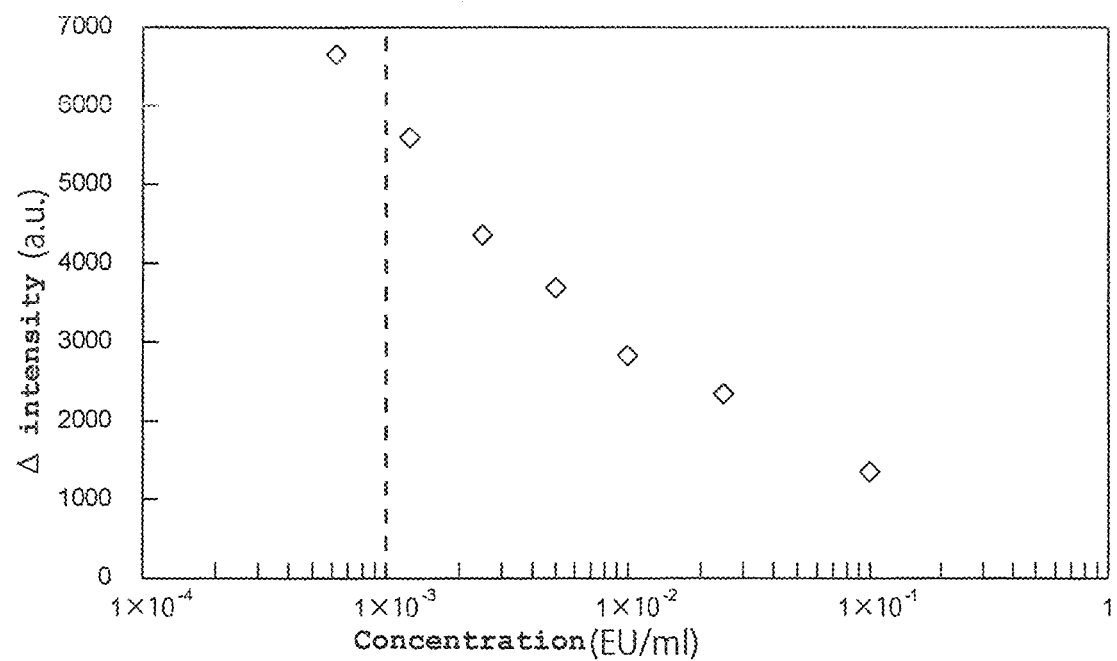

[FIG. 16]
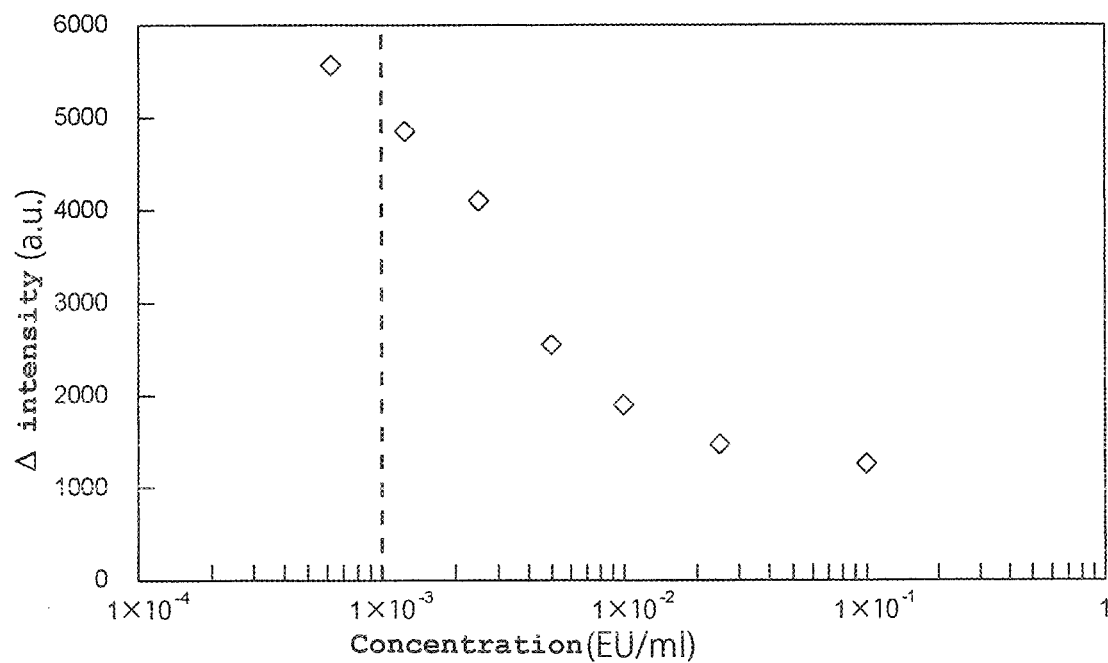
[FIG. 17]
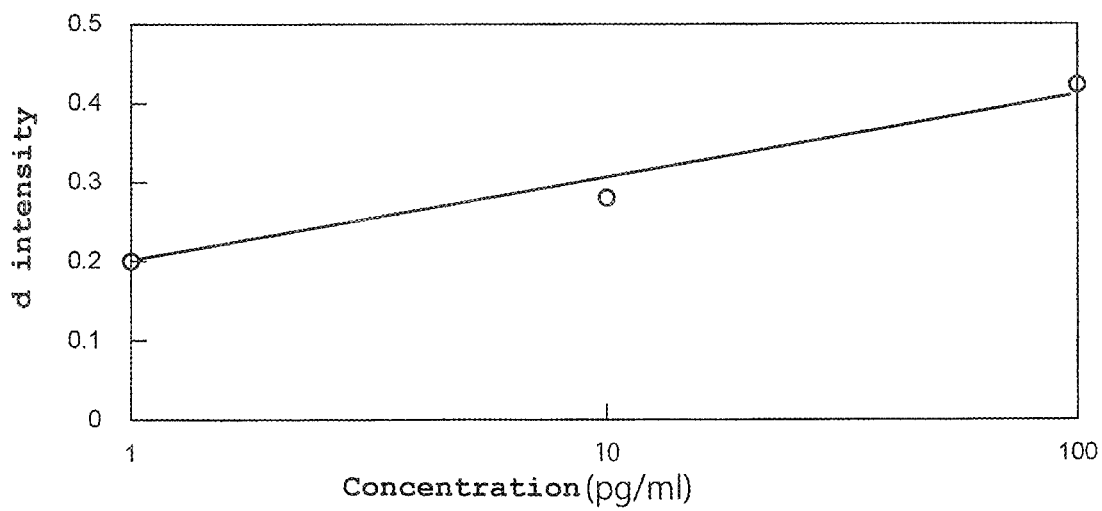

[FIG. 18]
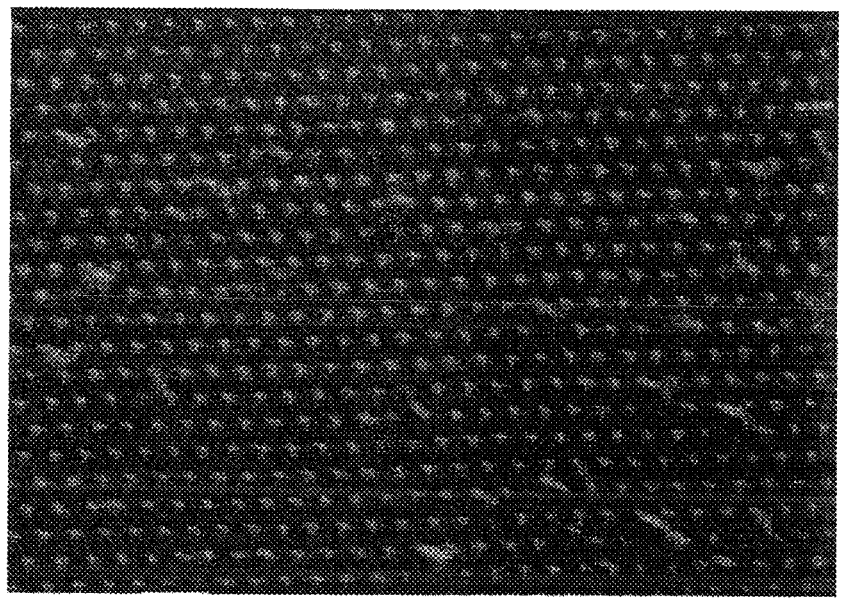

IMPLEMENT FOR INSPECTION, INSPECTING DEVICE AND INSPECTING METHOD

TECHNICAL FIELD

The present invention relates to an implement for inspection and an inspecting device used for measuring the concentration of a chemical substance. The present invention also relates to an inspecting method using the above-described implement for inspection.

BACKGROUND

A method of measuring the concentration of a substance derived from a living organism such as endotoxin using LAL reagent is known.

For example, in the inspecting method disclosed in the following Patent Document 1, a gel-like film is formed by reacting LAL reagent with endotoxin. The concentration of endotoxin is measured by measuring the thickness of the gel-like film by an interference enhanced reflection method (IER method).

In the inspecting method disclosed in the following Patent Document 2, a sample containing a coagulin monomer, produced by reacting LAL reagent with endotoxin, or an aggregate thereof is irradiated with light. The endotoxin concentration is measured by measuring the intensity of scattered light from the coagulin monomer or the aggregate thereof.

RELATED ART DOCUMENT

Patent Documents

Patent Document 1: JP 2007-327946 A
Patent Document 2: JP 2010-032436 A

SYSTEM OF THE INVENTION

Problems to be Solved by the Invention

In recent years, it has been required to more accurately measure the concentration of a substance derived from a living organism such as endotoxin. In the conventional method, it is difficult to measure, for example, the concentration of endotoxin or the like of 0.001 EU/ml or less with high accuracy.

An object of the present invention is to provide an implement for inspection and an inspecting device capable of measuring the concentration of a test substance with high accuracy. A further object of the present invention is to provide an inspecting method using the above-described implement for inspection.

Means for Solving the Problems

According to a broad aspect of the present invention, there is provided an implement for inspection used for measuring the concentration of a test substance. The implement for inspection includes a compound for reacting with the test substance to form a granular substance or comprise a compound which is for being bound to the test substance and is a granular substance, and a wall portion having a periodic structure on its surface.

In a specific aspect of the implement for inspection according to the present invention, the compound is not in contact with the periodic structure in the wall portion, and is disposed at a position distant from the periodic structure in the wall portion.

In a specific aspect of the implement for inspection according to the present invention, the compound is disposed on a surface of the periodic structure.

In a specific aspect of the implement for inspection according to the present invention, when the implement for inspection includes the compound for reacting with the test substance to form the granular substance, the compound for reacting with the test substance to form the granular substance is a compound for reacting with the test substance to form a granular substance in an aggregated state, and when the implement for inspection includes the compound which is for being bound to the test substance and is the granular substance, the compound which is for being bound to the test substance and is the granular substance is bound to the test substance to form a granular substance in an aggregated state.

In a specific aspect of the implement for inspection according to the present invention, the implement for inspection includes a compound which is for being bound to the test substance and is a granular substance, the test substance has an antigen, and the compound has an antibody.

In a specific aspect of the implement for inspection according to the present invention, the implement for inspection includes a compound for reacting with the test substance to form a granular substance, the test substance is glycolipid, and the compound is an enzyme for reacting with glycolipid.

In a specific aspect of the implement for inspection according to the present invention, the implement for inspection includes the compound for reacting with the test substance to form a granular substance, the test substance is endotoxin, and the compound is LAL reagent.

According to a broad aspect of the present invention, there is provided an inspecting device including the above-described implement for inspection, a light source for applying light to the bottom portion having the periodic structure of the implement for inspection, and a measuring instrument for measuring intensity of light emitted from the light source and reflected by the wall portion having the periodic structure.

According to a broad aspect of the present invention, there is provided an inspecting method using the above-described implement for inspection, the inspecting method including a step of applying light to the periodic structure to measure reference light intensity in a state where the test substance is not introduced into the implement for inspection, a step of applying light to the periodic structure to measure evaluation light intensity in a state where the test substance is introduced into the implement for inspection and the granular substance is deposited on the periodic structure, and a step of acquiring a relative value of the reference light intensity and the evaluation light intensity. In this inspecting method, when the relative value obtained when a sample in which a concentration of the test substance is known is introduced into the implement for inspection is compared to the relative value obtained when a sample in which a concentration of the test substance is unknown is introduced into the implement for inspection, the concentration of the test substance in the sample in which the concentration of the test substance is unknown is determined.

Effect of the Invention

An implement for inspection according to the present invention includes a compound capable of reacting with a test substance to form a granular substance or a compound which is capable of being bound to the test substance and is a granular substance, and further includes a wall portion having a periodic structure on its surface; therefore, the concentration of the test substance can be measured with high accuracy.

BRIEF DESCRIPTION OF DRAWINGS

FIG. 1 is a front cross-sectional view of an implement for inspection according to a first embodiment of the present invention.

FIG. 2 is a plan view of the implement for inspection according to the first embodiment of the present invention.

FIG. 3 is an enlarged front cross-sectional view of an implement for inspection according to a second embodiment of the present invention.

FIG. 4 is a front cross-sectional view of an implement for inspection according to a third embodiment of the present invention.

FIG. 5 is a plan view of the implement for inspection according to the third embodiment of the present invention.

FIG. 6 is an enlarged front cross-sectional view of an implement for inspection according to a fourth embodiment of the present invention.

FIG. 7 is a front cross-sectional view for describing an example of an inspecting method using the implement for inspection according to the first embodiment of the present invention.

FIG. 8 is an enlarged front cross-sectional view for describing an example of the inspecting method using the implement for inspection according to the first embodiment of the present invention.

FIG. 9 is an enlarged front cross-sectional view for describing an example of the inspecting method using the implement for inspection according to the first embodiment of the present invention.

FIG. 10 is an enlarged front cross-sectional view for describing an example of the inspecting method using the implement for inspection according to the first embodiment of the present invention.

FIG. 11 is an enlarged front cross-sectional view for describing an example of an inspecting method using the implement for inspection according to the fourth embodiment of the present invention.

FIG. 12 is an enlarged front cross-sectional view for describing a modified example of the inspecting method shown in FIG. 11.

FIG. 13 is a schematic diagram of an inspecting device according to a fifth embodiment of the present invention.

FIG. 14 is a schematic diagram of an inspecting device according to a sixth embodiment of the present invention.

FIG. 15 is a view showing a relationship between the concentration of endotoxin and Δ intensity in Example 1.

FIG. 16 is a view showing a relationship between the concentration of endotoxin and Δ intensity in Example 2.

FIG. 17 is a view showing a relationship between the concentration of cystatin C and d intensity in Example 3.

FIG. 18 is an SEM photograph of a surface of a periodic structure after measurement of cystatin C in Example 3.

MODE(S) FOR CARRYING OUT THE INVENTION

Hereinafter, the present invention will be described in detail.

An implement for inspection according to the present invention is used for measuring the concentration of a test substance. The implement for inspection according to the present invention includes a compound (first compound) which is capable of reacting with a test substance to form a granular substance, or a compound (second compound) which is capable of being bound to the test substance and is a granular substance. The implement for inspection according to the present invention may include the compound which is capable of reacting with a test substance to form a granular substance or the compound which is capable of being bound to the test substance and is a granular substance. The implement for inspection according to the present invention further includes a wall portion. The wall portion has a periodic structure on its surface.

In the implement for inspection, the test substance and the compound can be reacted or bound. A granular substance formed by reacting the test substance with the compound or a granular substance in which the test substance is bound to the compound can be deposited on the wall portion, so that the granular substance can be deposited on the periodic structure. In a state where the granular substance is deposited on the periodic structure, the intensity of reflected light occurring when the wall portion is irradiated with light greatly changes as compared with a state where the granular substance is not deposited on the periodic structure. Accordingly, it is possible to improve accuracy of measuring the concentration of the test substance.

The granular substance formed by reacting the test substance with the compound or the granular substance in which the test substance is bound to the compound may not be in an aggregated state. In a conventional concentration measurement, light scattering due to aggregates is detected, and therefore, it is considered that measurement is difficult especially when the concentration is low. That is, it is considered that light scattering cannot be detected until aggregates reach a certain size (for example, micrometer order), or accuracy is low because a degree of aggregation varies. In the present invention, it is found that presence of a granular substance, such as a reaction product between a test substance and a compound, on the surface of a fine periodic structure (for example, nanometer order) changes an optical response (for example, reflected light intensity) from the surface of the periodic structure, and when the granular substance is not in an aggregated state, the concentration can be measured with higher accuracy even if the concentration of the test substance is low. In addition, the concentration can be measured more quickly than before.

The compound is not in contact with the periodic structure in the wall portion, and may be disposed at a position distant from the periodic structure in the wall portion. In this case, the test substance and the compound can be reacted or bound at a position distant from the periodic structure. The granular substance can be reliably deposited by the periodic structure by gravity or the like. The compound may be disposed on the surface of the periodic structure in the wall portion. In this case, the change in the optical response from the periodic structure can be detected more quickly.

As a compound capable of reacting with the test substance to form a granular substance, a compound which reacts with the test substance to be gelled can be used, for example.

Hereinafter, specific embodiments of the present invention will be described with reference to the drawings.

FIG. 1 is a front cross-sectional view of an implement for inspection according to a first embodiment of the present invention. FIG. 2 is a plan view of the implement for inspection according to the first embodiment of the present invention. FIG. 1 is a cross-sectional view of the implement for inspection taken along the line A-A of FIG. 2.

The drawings referred to in the embodiments are illustrated schematically, and the dimensional ratio and the like of objects depicted in the drawings are different from those of actual objects in some cases. The specific dimensional ratio and the like of objects should be determined with the following description taken into consideration. In particular, in the drawings referred to, recesses are shown in an enlarged manner for convenience of illustration. Actual recesses are nano-sized and finer.

An implement 1 for inspection shown in FIGS. 1 and 2 includes a compound 6 capable of reacting with a test substance to form a granular substance, and a wall portion. In the present embodiment, the wall portion is a bottom portion 3 of the implement 1 for inspection. The bottom portion 3 has a periodic structure 3A on its surface. In place of the compound 6 capable of forming a granular substance, a compound which is capable of being bound to the test substance and is a granular substance may be used.

The implement 1 for inspection is provided with a side wall portion 4 erected from the bottom portion 3 at the side of the periodic structure 3A in the bottom portion 3. The bottom portion 3 and the side wall portion 4 constitute a container for inspection. The container 1 for inspection has a storage portion 2 surrounded by the bottom portion 3 and the side wall portion 4. A granular substance formed by reacting the test substance with the compound 6 and a reaction solution obtained by reacting the test substance with the compound 6 can be stored in the storage portion 2.

The implement 1 for inspection is provided with a lid 5 disposed on the side opposite to the bottom portion 3 side of the side wall portion 4. The compound 6 is disposed on the surface of the lid 5. When a liquid containing the test substance is stored in the storage portion 2, since the lid 5 is disposed on the storage portion 2, the liquid and the compound 6 can be brought into contact with each other in the storage portion 2. Thus, the test substance and the compound 6 can be easily reacted with each other. In the present embodiment, the compound 6 is disposed above the periodic structure 3A.

The implement 1 for inspection is a microchip in which the bottom portion 3, the side wall portion 4, and the lid 5 are stacked. As shown in FIG. 2, an introduction portion 7 is provided. The introduction portion 7 corresponds to a portion where the side wall portion 4 is not provided. The liquid containing the test substance can be introduced into the storage portion 2 through the introduction portion 7. The lid may be provided with the introduction portion. The implement for inspection may have a micro flow path connected to the introduction portion 7, and may have, for example, a space for pretreatment of the test substance, a waste liquid path, and the like.

As described later, the concentration of the test substance in the liquid can be measured by irradiating the bottom portion with light for inspection and measuring the intensity of light reflected from the bottom portion. The lid is preferably transparent from the viewpoint of transmitting the inspection light therethrough. A material of the bottom portion, the side wall portion, and the lid of the implement for inspection is not particularly limited, and examples thereof include resin and glass.

The periodic structure 3A has a plurality of recesses 3a. In the present embodiment, the recess 3a has a columnar shape.

The recesses 3a are regularly arranged. In the present embodiment, the recesses 3a are arranged in a plurality of rows at equal intervals in a first direction (vertical direction in FIG. 2) and a second direction (horizontal direction in FIG. 2) orthogonal to the first direction. The recess 3a has a two-dimensional periodic structure.

In the periodic structure, a plurality of recesses may be regularly arranged, or a plurality of protrusions may be regularly arranged.

The shape and arrangement of the protrusions or recesses can be appropriately changed according to the direction and angle of irradiation of the inspection light. The tip of the protrusion or recess may be a flat surface, a curved surface, or a point-like shape. The protrusion or recess may have a groove-like shape. For example, the shape of the protrusion or recess may be a prismatic, pyramidal or conical. The periodic structure may be a one-dimensional periodic structure.

The period of the periodic structure is not particularly limited, and is preferably 1000 nm or less. The period of the periodic structure is preferably the particle size of a granular substance or more. The period of the periodic structure is, for example, an interval between the tip of each protrusion or recess (the center in the case where the tip is a flat surface or the like) and the tip of the protrusion or recess (the center in the case where the tip is a flat surface) most adjacent thereto.

An opening area between the protrusions or an opening area of the recess is preferably 640000 $nm^2$ or less, and more preferably 160000 $nm^2$ or less. The opening area between the protrusions or the opening area of the recess is preferably 2500 $nm^2$ or more, and more preferably 10000 $nm^2$ or more. The height of the protrusion or the depth of the recess is preferably 800 nm or less, and more preferably 400 nm or less. The height of the protrusion or the depth of the recess is preferably 50 nm or more, and more preferably 100 nm or more. Although the shape and size of each protrusion or recess can be set arbitrarily, they can be determined by the type of a granular substance formed by reacting a test substance with a compound and the shape of the recess. The reflected light intensity can be optimized by adjusting the period of the periodic structure and the shape and size of the protrusion or recess.

It is sometimes difficult to perfectly match a plurality of opening areas and the heights of a plurality of protrusions or the depths of a plurality of recesses. The period of the periodic structure may vary as long as there is no significant influence on the accuracy of concentration measurement. From the viewpoint of effectively reducing noise in measurement, standard deviation of the opening areas between the protrusions or the opening areas of the recesses in the periodic structure is preferably 10% or less, and more preferably 5% or less.

Examples of the test substance include sugar chain, glycolipid, protein, peptide, and DNA. Examples of the sugar chain include Mac-2 binding protein sugar chain. Examples of the glycolipid include endotoxin, peptide glucan, and β-D-glucan. Examples of the protein include a tumor marker, urine protein, and amyloid. Examples of the tumor marker include PSA which is a marker of prostate cancer, CEA which is a marker of colon cancer, CA 15-3 which is a marker of breast cancer, and AEP which is a marker of lung cancer. Examples of the peptide include brain natriuretic peptide (BNP) and atrial natriuretic peptide (ANP).

Examples of the compound in the present invention include an enzyme, a support with an antibody, and a support with complementary DNA. Examples of the enzyme include LAL reagent. Examples of the support with an antibody include latex with an antibody and metal nanoparticles with an antibody.

For example, when the test substance is glycolipid, a compound capable of reacting with glycolipid to form a granular substance may be an enzyme capable of reacting with glycolipid.

In the implement 1 for inspection, the test substance is endotoxin, and the compound 6 is LAL reagent. The compound 6 reacts with the test substance to form a granular substance of gel. In the implement 1 for inspection, a distance between the recesses 3a is 460 nm. By depositing a granular substance in the recess 3a, the intensity of light reflected from the bottom portion 3 can be greatly changed. Specifically, in the implement 1 for inspection, the intensity of the light reflected from the bottom portion 3 can be significantly reduced. Accordingly, the concentration of a low-concentration test substance can be measured with high accuracy.

The size of the recess corresponds to the opening area (the opening area of the recess) at an opening end of the recess. The size between the protrusions corresponds to the opening area (the opening area between the protrusions) at an opening end between the protrusions. The size of the recess and the size of the space between the protrusions may be smaller than the size of the granular substance. In this case, the granular substance covers the periodic structure. It is possible to greatly change the intensity of the light reflected from the bottom portion of the implement for inspection.

The test substance may have an antigen, or may be an antigen which is a marker or the like. In this case, the compound preferably has an antibody. The compound described above may be, for example, latex with an antibody or the like. The antibody can be bound to the antigen. A granular substance in an aggregated state can be formed by binding the test substance and the compound. The intensity of the light reflected from the bottom portion of the implement for inspection can be greatly changed even when the granular substance in the aggregated state covers the periodic structure.

The periodic structure 3A may be provided at a portion of the bottom portion 3. It is preferable that the periodic structure 3A is provided at least at a position facing the compound 6. In this case, a granular substance (a granular substance or the like formed by reacting the test substance with the compound 6) can be efficiently deposited in the periodic structure 3A by gravity.

The periodic structure can be shaped, for example, at the time of molding the storage portion. After the storage portion having no periodic structure is obtained, the surface of the storage portion is subjected to shaping processing, whereby the periodic structure may be formed.

The wall portion having the periodic structure may be the side wall portion of the implement for inspection. In this case, a granular substance can be deposited in the periodic structure, for example, by electrophoresis or the like.

FIG. 3 is an enlarged front cross-sectional view of an implement for inspection according to a second embodiment of the present invention.

The implement for inspection of the present embodiment includes a compound 36 capable of reacting with a test substance to form a granular substance, and a wall portion. The wall portion is a bottom portion 33 of the implement for inspection. The bottom portion 33 has a periodic structure 33A on its surface. In the periodic structure 33A, a plurality of recesses 33a are regularly arranged. The implement for inspection of the present embodiment is different from the implement 1 for inspection in that the compound 36 is disposed on the surface of the periodic structure 33A. The wall portion having the periodic structure may be the side wall portion of the implement for inspection. In place of the compound 36 capable of forming a granular substance, a compound which is capable of being bound to the test substance and is a granular substance may be used. However, in the implement for inspection of FIG. 3, it is preferable to use the compound 36 capable of forming a granular substance.

In the present embodiment, the granular substance is formed on the surface of the periodic structure 33A. Thus, it is possible to effectively shorten the time from the start of the reaction until a state in which the intensity of light reflected from the bottom portion 33 greatly changes is achieved.

FIG. 4 is a front cross-sectional view of an implement for inspection according to a third embodiment of the present invention. FIG. 5 is a plan view of the implement for inspection according to the third embodiment of the present invention. FIG. 4 is a cross-sectional view of the implement for inspection taken along the line B-B of FIG. 5.

The implement 11 for inspection includes a petri dish and a lid 15. The petri dish has a wall portion with a periodic structure 13A formed on its surface. In the periodic structure 13A, a plurality of recesses 13a are regularly arranged. The wall portion is a bottom portion 13 of the petri dish. The petri dish further includes a side wall portion 14 erected from an outer peripheral edge of the bottom portion 13.

In the implement 11 for inspection, the bottom portion 13 and the side wall portion 14 are integrally constituted, and are configured as one instrument (container). The implement 11 for inspection has a storage portion 12 surrounded by the bottom portion 13 and the side wall portion 14.

In the implement 11 for inspection, after a liquid containing the test substance is stored in the storage portion 12, the lid 15 is installed on the storage portion 12, whereby the reaction between the test substance and the compound 6 can be started.

After a liquid not containing the test substance is stored in the storage portion 12, the test substance may be introduced into the storage portion 12. Light irradiation for measurement of the concentration of the test substance in the liquid may be performed in a state where the lid is removed. In this case, the lid may not be transparent.

FIG. 6 is an enlarged front cross-sectional view of an implement for inspection according to a fourth embodiment of the present invention.

The implement for inspection of the present embodiment includes a compound 56 capable of being bound to a test substance, an antibody 57, and a wall portion. The compound 56 has an antibody. The compound 56 is, for example, latex with an antibody, and is a granular substance. In the present embodiment, it is assumed that an antigen to be bound to the compound 56 is used as the test substance. The antibody 57 is preferably the same as the antibody possessed by the compound 56. In FIG. 6, the antibody is schematically indicated by a Y shape.

The wall portion is a bottom portion 3 of the implement for inspection. The bottom portion 3 has a periodic structure 3A on its surface. In the periodic structure 3A, a plurality of recesses 3a are regularly arranged. The implement for inspection is provided with a side wall portion erected from the bottom portion 3 at the side of the periodic structure 3A in the bottom portion 3. The implement for inspection has a storage portion surrounded by the bottom portion 3 and the side wall portion. The wall portion having the periodic structure may be the side wall portion of the implement for inspection.

The implement for inspection of the present embodiment has a liquid W disposed in the storage portion. The compound 56 is contained in the liquid W. The antibody 57 is disposed only on a protrusion of the periodic structure 3A. At the time of inspection, the test substance can be bound to the compound 56, and, at the same time, the test substance can be bound to the antibody 57.

In the present embodiment, the test substance bound to the compound 56 can be selectively deposited on the protrusion. Due to the deposition of the test substance in this state, a refractive index greatly changes at the protrusion, so that the intensity of light reflected from the bottom portion of the implement for inspection can be greatly changed.

The above compound may be disposed in the same manner as in the first embodiment. The implement for inspection may not have the antibody 57. Also in this case, the refractive index can be greatly changed by deposition in the periodic structure of a granular substance in which the test substance and the compound are bound.

In the present embodiment, the period of the periodic structure 3A is approximately the same as a wavelength of light to be measured. In a medium having a relatively large change in the refractive index in a period substantially equal to a wavelength of light, light in a specific wavelength region cannot enter and is reflected, and light having a wavelength outside the specific wavelength region transmits. The wavelength region of light that cannot enter the medium as described above is called a photonic band gap. A photonic band gap is generated in the periodic structure 3A by suitably setting an angle of light to be applied. At the time of inspection, a peak of reflected light occurs in the wavelength region of the photonic band gap. Since the peak intensity greatly changes due to the change in the refractive index, measurement accuracy can be further enhanced. In addition, the concentration of a low-concentration test substance can be measured.

An example of an inspecting method using the implement 1 for inspection shown in FIG. 1 will be described with reference to FIGS. 7 to 9.

FIG. 7 is a front cross-sectional view for describing an example of the inspecting method using the implement for inspection according to the first embodiment of the present invention. FIG. 8 is an enlarged front cross-sectional view for describing an example of the inspecting method using the implement for inspection according to the first embodiment of the present invention. FIG. 9 is an enlarged front cross-sectional view for describing an example of the inspecting method using the implement for inspection according to the first embodiment of the present invention.

This inspecting method includes (1) a step of measuring reference light intensity, (2) a step of measuring evaluation light intensity, and (3) a step of acquiring a relative value of the reference light intensity and the evaluation light intensity. The steps (1) to (3) may be performed in this order, or in the order of (2), (1), and (3).

In this inspecting method, the steps of (1) to (3) are performed on a sample in which the concentration of a test substance is known, and a calibration curve is prepared in advance. For example, a plurality of relationships between the (known) concentration of the test substance and the relative value obtained in the above step are plotted to create approximate straight lines and approximate expressions. Similarly, the steps (1) to (3) are performed on a sample in which the concentration of the test substance is unknown, and the obtained relative value is substituted into the approximate straight line or the approximate expression, so that the concentration of the test substance in the unknown sample can be determined.

An example of the steps (1) to (3) will be described in detail below.

(1) In the step of measuring the reference light intensity, in a state where a test substance is not introduced into the implement 1 for inspection, the periodic structure 3A is irradiated with light, and reflected light intensity is measured. For example, in a state where a liquid not containing the test substance is stored in the storage portion 2, light for inspection can be applied, and the intensity of light reflected from the bottom portion 3 can be measured. In this case, as the liquid not containing the test substance, the same fluid or solvent as a sample containing the test substance can be used.

(2) In the step of measuring the evaluation light intensity, in a state where a test substance is introduced into the implement for inspection and a granular substance (such as a granular substance as a reaction product between the test substance and a compound) is deposited on the periodic structure 3A, the periodic structure 3A is irradiated with light, and reflected light intensity is measured. Specifically, as shown in FIG. 7, a liquid X containing the test substance is stored in the storage portion 2. The reaction between the test substance and the compound 6 is started by bringing the liquid X and the compound 6 into contact with each other. As shown in FIG. 8, a granular substance Y is formed by the reaction between the test substance and the compound 6. The granular substance Y is deposited in the recess 3a at the bottom portion 3 by gravity.

Then, as shown in FIG. 9, inspection light L1 is applied to the bottom portion 3 having the recess 3a in which the granular substance Y is deposited. Then, the intensity of light L2 reflected from the bottom portion 3 is measured.

Deposition of the granular substance Y in the recesses 3a reduces the intensity of light applied to the bottom portion 3 and reflected by the bottom portion 3. Accordingly, it is possible to improve the accuracy of measuring the concentration of the test substance.

After the liquid containing the test substance is removed, the inspection light L1 may be applied to the bottom portion 3, and the intensity of the light L2 reflected from the bottom portion 3 may be measured.

(3) In the step of acquiring the relative value of the reference light intensity and the evaluation light intensity, a value of a difference between the reference light intensity and the evaluation light intensity is calculated. The relative value may be obtained using a value of a ratio between the reference light intensity and the evaluation light intensity. A value obtained by appropriately applying a mathematical operation to the difference or the ratio may be set as the relative value.

The reflected light intensity may be measured only with a specific wavelength, and the reflected light intensity may be acquired as a spectrum at a plurality of consecutive wavelengths. Although any wavelength can be selected for a wavelength of light to be applied, the wavelength can be appropriately selected according to the shape and size of the periodic structure. Although visible light can be typically used, infrared or ultraviolet light can also be used.

In the above description, as the reference light intensity and the evaluation light intensity, the case of measuring reflected light when the periodic structure is irradiated with light has been described. However, transmitted light may be measured. As long as a change in optical response from the surface of the periodic structure can be detected, not direct reflected light or transmitted light but light to which some optical operation is applied may be detected.

FIG. 10 is an enlarged front cross-sectional view for describing an example of the inspecting method using the implement for inspection according to the first embodiment of the present invention.

As shown in FIG. 10, in a state where the height at which the granular substance Y is deposited in the recess 3a is lower than the depth of the recess 3a (the height of the side surface of the recess 3a), the intensity of the light L2 reflected by the bottom portion 3 may be measured. Even in a state where the height at which the granular substance Y is deposited in the recess 3a does not reach the depth of the recess 3a (the height of the side surface of the recess 3a), the intensity of the light L2 reflected by the bottom portion 3 becomes low. Accordingly, the concentration of a low-concentration test substance can be measured. In addition, the inspection time can be shortened.

From the viewpoint of further improving the accuracy of measurement, a filling rate of the granular substance Y in the recess 3a at the time of measurement is preferably 1% or more, more preferably 10% or more, still more preferably 30% or more, even more preferably 50% or more, further more preferably 70% or more, particularly preferably 90% or more, most preferably 95% or more. The filling rate is the volume of the granular substance in the volume of the recess. When the granular substance is deposited between the protrusions, the volume of the granular substance in the volume between the protrusions is the filling rate.

FIG. 11 is an enlarged front cross-sectional view for describing an example of an inspecting method using the implement for inspection according to the fourth embodiment of the present invention.

As shown in FIG. 11, a test substance Z1 in this inspecting method is an antigen bound to the antibody 57 and the antibody possessed by the compound 56. The test substance Z1 is bound to the compound 56 contained in the liquid W. The compound 56 is a granular substance. The test substance Z1 bound to the compound 56 is bound to the antibody 57 disposed at the protrusion of the periodic structure 3A and selectively deposited on the protrusion. Consequently, a refractive index of a portion irradiated with the inspection light changes greatly. In this inspecting method, the wavelength of the inspection light and the period of the periodic structure 33A are substantially equal to each other, and a peak of light reflected at the photonic band gap occurs. The intensity of the peak of the reflected light greatly changes due to the change in the refractive index. In the present inspecting method utilizing the photonic band gap, it is possible to measure the concentration of a test substance having an extremely low concentration of approximate 100 pg/ml or less.

As with the first embodiment, an implement for inspection in which the above-described compound is disposed at a position distant from the periodic structure may be used. In this case, as shown in FIG. 12, the test substances Z1 are bound to each other via the compound 56 as a granular substance to form an aggregate Z2. The granular substance thus aggregated is deposited in the periodic structure 33A. Also in this case, the refractive index of the portion irradiated with the inspection light changes greatly. Also in the case shown in FIG. 12, the concentration of a low-concentration test substance can be measured.

FIG. 13 is a schematic diagram of an inspecting device according to a fifth embodiment of the present invention.

An inspecting device 20 includes the implement 11 for inspection of the third embodiment, a light source 28, and a measuring instrument 29. Light L1 is applied from the light source 28 to the bottom portion having the recesses of the implement 11 for inspection. The intensity of light L2 reflected by the bottom portion is measured by the measuring instrument 29. The inspecting device 20 can measure the concentration of a test substance with high accuracy by the above-described inspecting method.

FIG. 14 is a schematic diagram of an inspecting device according to a sixth embodiment of the present invention.

An inspecting device 40 includes the implement 1 for inspection of the first embodiment, an installation portion 44 in which the implement 1 for inspection is installed, a light source 28, and a measuring instrument 29.

The installation portion 44 has a flow path 47 through which a liquid containing a test substance is sent. The flow path 47 is connected to the introduction portion 7 of the implement 1 for inspection. A reaction between the test substance and a compound can be started by introducing the liquid containing the test substance into the storage portion of the implement 1 for inspection through the flow path 47. The concentration of the test substance can be measured with high accuracy by the above-described inspecting method. The inspection can be easily performed by installing the implement 1 for inspection in the installation portion 44.

The above-described implement for inspection may be a microfluidic device, and the microfluidic device may include a compound capable of forming a granular substance or a compound which is capable of being bound to the test substance and is a granular substance, and a wall portion. The compound may be disposed in a microchannel in the microfluidic device. The wall portion may be an inner wall portion of the microchannel in the microfluidic device. The inspecting device may be a microfluidic device including the light source and the measuring instrument described above.

Hereinafter, the present invention will be described in more detail based on specific examples.

Example 1

The implement for inspection of the third embodiment was used to determine a relationship between the concentration of endotoxin and intensity of reflected light at the bottom portion of the implement for inspection.

The implement for inspection of the third embodiment was prepared. The recess had a cylindrical shape, and had a diameter of 230 nm and a plane area (opening area) of $41.5 \times 10^3$ nm$^2$. A distance between the recesses was 460 nm, and the depth of the recess was 200 nm.

Then, blank data (reference light intensity) was acquired. In measurement for acquiring the blank data, the bottom portion of the implement for inspection was irradiated with light, and the intensity of light reflected by the bottom portion was measured, whereby the blank data was acquired.

Then, a liquid containing endotoxin and water was prepared. The endotoxin concentrations in the liquid containing endotoxin and water were 0.000625 EU/ml, 0.00125 EU/ml, 0.0025 EU/ml, 0.005 EU/ml, 0.01 EU/ml, 0.025 EU/ml, 0.05 EU/ml, and 0.1 EU/ml, respectively.

Then, LAL reagent (manufactured by Lonza Ltd.) was placed on the lid. Then, the liquid containing endotoxin and water was stored in the storage portion of the implement for inspection. Then, the lid was disposed on the storage portion, and the implement for inspection was left to stand for 60 minutes. Then, the liquid containing endotoxin and water was removed. Then, the bottom portion of the implement for inspection was irradiated with light, and the intensity (evaluation light intensity) of light reflected by the bottom portion was measured.

Then, Δ intensity in each liquid containing endotoxin and water was determined. The Δ intensity is a difference between the intensity of the light reflected by the bottom portion and the blank data. Similarly, the Δ intensity when water was stored in the storage portion was determined.

FIG. 15 is a view showing a relationship between the endotoxin concentration and the Δ intensity in Example 1.

As shown in FIG. 15, it is found that at the endotoxin concentration of 0.000625 EU/ml or more, the Δ intensity decreases as the endotoxin concentration increases. Thus, according to the present invention, it is found that high-precision inspection can be performed at a concentration around 0.001 EU/ml, and that inspection can be performed even within a concentration range lower than 0.001 EU/ml.

Example 2

The relationship between the endotoxin concentration and the intensity of the reflected light at the bottom portion of the implement for inspection was determined in the same manner as in Example 1 except that LAL reagent (manufactured by Wako Pure Chem. Ind. Ltd.) was used as the above compound.

FIG. 16 is a view showing a relationship between the endotoxin concentration and the Δ intensity in Example 2.

As shown in FIG. 16, as in Example 1, it is found that at the endotoxin concentration of 0.000625 EU/ml or more, the Δ intensity decreases as the endotoxin concentration increases.

Example 3

The implement for inspection of the fourth embodiment was used to determine a relationship between the concentration of cystatin C and the intensity of the reflected light at the bottom portion of the implement for inspection.

The implement for inspection of the fourth embodiment was prepared. The protrusion in the periodic structure had a cylindrical shape and had a diameter of 230 nm. A distance between the protrusions was 460 nm. The surface of the periodic structure was immersed in a cystatin C antibody aqueous solution for 24 hours. Then, washing with TBS-T buffer was performed three times. Then, the implement for inspection was dried. Thus, the periodic structure was modified with cystatin C antibody.

Then, a liquid containing cystatin C and physiological saline was prepared. The cystatin C concentrations in the liquid containing cystatin C and physiological saline were 0 pg/ml, 10 pg/ml, and 100 pg/ml, respectively.

Then, a cystatin C antibody modified latex aqueous solution (manufactured by Sekisui Medical Co., Ltd.) was placed on the lid. Then, the cystatin C antibody modified latex aqueous solution was stored in the storage portion of the implement for inspection. Then, the reflected light intensity immediately after adding the liquid containing cystatin C and physiological saline (0 minutes) and the reflected light intensity after standing for 10 minutes were measured. The implement for inspection was irradiated with light at an angle of 15°, and the intensity (evaluation light intensity) of the reflected light was measured.

Then, d intensity in each liquid containing cystatin C and water was determined. The d intensity is a difference between the reflected light intensity immediately after adding a liquid (0 minutes) and the reflected light intensity after standing for 10 minutes. Similarly, the Δ intensity when water was stored in the storage portion was determined.

FIG. 17 is a view showing a relationship between the cystatin C concentration and the d intensity in Example 3.

As shown in FIG. 17, it is found that at the cystatin C concentration of 10 pg/ml or more, the d intensity increases as the cystatin C concentration increases. Thus, according to the present invention, it is found that high-precision inspection can be performed at a concentration around 10 pg/ml, and inspection can be performed even within an extremely low concentration range.

FIG. 18 is an SEM photograph (using trade name "VE-8800" manufactured by Keyence Corporation) of 10 pg/ml cystatin C in Example 3, and it is found that cystatin C antibody modified latex is adsorbed to the protrusions in the periodic structure.

EXPLANATION OF SYMBOLS

1: implement for inspection
2: storage portion
3: bottom portion
3A: periodic structure
3a: recess
4: side wall portion
5: lid
6: compound
7: introduction portion
11: implement for inspection
12: storage portion
13: bottom portion
13A: periodic structure
13a: recess
14: side wall portion
15: lid
20: inspecting device
28: light source
29: measuring instrument
33: bottom portion
33A: periodic structure
33a: recess
36: compound
40: inspecting device
44: installation portion
47: flow path
56: compound
57: antibody

The invention claimed is:

1. An implement for inspection used for measuring a concentration of a test substance, the implement for inspection comprising:
   a compound for reacting with the test substance to form a granular substance or a compound which is for being bound to the test substance and is a granular substance; and
   a wall portion having a periodic structure on a surface of the wall portion,
   wherein the compound is not in contact with the periodic structure in the wall portion, and is disposed at a position distant from the periodic structure in the wall portion,
   the granular substance formed by reacting the test substance with the compound or a granular substance in which the test substance is bound to the compound is deposited on the periodic structure, and the periodic structure generates a peak of reflected light in the wavelength region of a photonic band gap when light is applied to the periodic structure.

2. The implement for inspection according to claim 1, wherein when the implement for inspection includes the compound for reacting with the test substance to form the granular substance, the compound for reacting with the test substance to form the granular substance is a compound for reacting with the test substance to form a granular substance in an aggregated state, and when the implement for inspection includes the compound which is for being bound to the test substance and is the granular substance, the compound which is for being bound to the test substance and is the granular substance is bound to the test substance to form a granular substance in an aggregated state.

3. The implement for inspection according to claim 1, comprising the compound which is for being bound to the test substance and is a granular substance, wherein the test substance has an antigen, and the compound has an antibody.

4. The implement for inspection according to claim 1, comprising the compound for reacting with the test substance to form a granular substance, wherein the test substance is glycolipid, and the compound is an enzyme for reacting with glycolipid.

5. The implement for inspection according to claim 1, comprising the compound for reacting with the test substance to form a granular substance, wherein the test substance is endotoxin, and the compound is LAL reagent.

6. An inspecting device comprising:

the implement for inspection according to claim 1;

a light source for applying light to the wall portion having the periodic structure of the implement for inspection; and a measuring instrument for measuring intensity of light emitted from the light source and reflected by the wall portion having the periodic structure.

7. An inspecting method using the implement for inspection according to claim 1, the inspecting method comprising:

a step of applying light to the periodic structure to measure reference light intensity in a state where the test substance is not introduced into the implement for inspection;

a step of applying light to the periodic structure to measure evaluation light intensity in a state where the test substance is introduced into the implement for inspection and the granular substance is deposited on the periodic structure; and a step of acquiring a relative value of the reference light intensity and the evaluation light intensity, wherein when the relative value obtained when a sample in which a concentration of the test substance is known is introduced into the implement for inspection is compared to the relative value obtained when a sample in which a concentration of the test substance is unknown is introduced into the implement for inspection, the concentration of the test substance in the sample in which the concentration of the test substance is unknown is determined.

8. The implement for inspection according to claim 1, wherein the periodic structure of the wall portion has a plurality of recesses or a plurality of protrusions and the periodic structure of the wall portion is a periodic structure by the plurality of recesses or the plurality of protrusions.

* * * * *